United States Patent [19]

Fischer

[11] Plant 5,191

[45] Feb. 14, 1984

[54] AFRICAN VIOLET PLANT

[75] Inventor: Arnold Fischer, Hanover, Fed. Rep. of Germany

[73] Assignee: Pan American Plant Company, Parrish, Fla.

[21] Appl. No.: 390,800

[22] Filed: Jun. 21, 1982

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

An African violet cultivar known by the cultivar name of Don Juan having semi-double to double lavender flowers carried on erect peduncles so as to position the profuse bouquet above the foliage.

4 Drawing Figures

The present invention comprises a new and distinct cultivar of African violet plant, botanically known as Saintpaulia hybrids, and hereinafter referred to by the cultivar name Don Juan.

The new cultivar was referred to during the breeding and selection process by the description V7-E57-F, and is a product of a planned breeding program. The basic objective of the program was to create a new African violet cultivar having semi-double lavender flowers formed in a relatively profuse bouquet well above attractive dark green foliage.

The new cultivar was originated from a cross made in a controlled breeding program in Hanover, West Germany. Both the female and male parents are at the present time unknown.

Don Juan was discovered and selected by me as a flowering plant within the progeny of the stated cross in a controlled environment in Fallbrook, Calif. Asexual reproduction of the new cultivar by leaf cuttings as performed by me at Fallbrook, Calif. has demonstrated the combination of characteristics as herein disclosed for the new cultivar are firmly fixed and are retained through successive generations of asexual reproduction.

Don Juan has not been observed under all possible environmental conditions. The phenotype may vary significantly with variations in environment such as temperature, light intensity, and day length. The following observations, measurements and values describe the new cultivar as grown under greenhouse conditions which closely approximate those used in commercial practice.

The following traits have been repeatedly observed and are determined to be the basic characteristics of Don Juan, which in combination distinguish this African violet as a new and distinct cultivar:

1. Relatively large semi-double to double flowers borne on erect peduncles.
2. Lavender flower color.
3. Relatively dark green foliage, which provides a pleasant contrast with the lavender flowers.
4. The location of the relatively profuse bouquet well above the foliage.
5. The plant may be finished under controlled conditions in 10–12 weeks from a 2¼" plant.

The accompanying photographic drawings show a typical specimen plant of the new cultivar, or its components. Sheet 1 comprises a color photograph in the form of a perspective view of the plant, showing principally the flower bouquet located above the foliage; a second color photograph showing individual blooms positioned adjacent a color chart which demonstrates accurate color values, and an enlarged black and white photo of a single bloom in plan view. The colors appearing in the photographs are as true as possible without color illustrations of this type. Sheet 2 comprises a black and white photograph showing the underside of individual leaves at various stages of growth or location on a typical plant.

In the following description, color references are made to The Royal Horticultural Society Colour Chart (RHS), except where general colors of ordinary significance are referred to. Color values were taken under indirect natural light conditions.

Botanical classification: Saintpaulia hybrids, cv. Don Juan.

*Parentage.*—Male parent: Unknown. Female parent: Unknown.

*Propagation.*—The new cultivar holds its distinguishing characteristics through successive propagations by leaf cuttings.

Plant: From 7 cm. to 11 cm. tall when grown in pots, with the general form being rounded, and the plant having a vigorous growth habit.

Leaves.—General form: Oval with cordate base and repand margin. Diameter: 4.5×5 cm. to 8.5×8.5 cm. Texture: Glossy. Veins: Pinnate. Color (Upperside): 147A. (Underside): 147C. Quantity: Abundant.

*Flowers.*—Buds: Approximately 1 cm. in diameter and length, and round in shape; normal opening, with the color of the petals when the sepals first divide 77A; when petals begin to unfurl, 77A. Sepals: Lanceolate in shape, 5 in number, color inside 183A, outside 183B; branched. Phyllaries: Lanceolate in shape, 2 in number, color 183A. Calyx: Relatively small, funnel-shaped, splits, hairy. Peduncles: Erect, 2–3 cm. in length, hairy, color 182B.

*Individual flowers.*—Size: Very large, diameter 4–4.5 cm., 2 cm. in depth. Color: (Spring) Upperside: body 77B, base, 77A. Underside: 77C. Borne: On strong and upright peduncles in clusters, with the blooms being cup-shaped when first opening and generally becoming flatter when maturing. Shape: Semi-double to double rotate zygomorphic, margin ruffled, apex rounded, with 5–10 petals per flower. Corolla: Profuse, positioned above the relatively dark green foliage thereby providing a pleasant contrast. Peduncle: 4–9 cm. when fully grown, strong and upright, color 182B.

*Flowering habit:* 10–12 weeks to finish in a controlled environment from a 2¼" plant, with the petals being sympetalous and persistant. Blooms last 2–3 weeks.

*Reproductive organs.*—Stamens: 3–5 in number, borne singly, surrounding ovary, anther basifixed. Anthers: 2–3 mm. in size, yellow in color. Filaments: 2–3 mm. in length, color insignificant. Pistils: 1 in number. Styles: 4–5 mm. in length, color 77B. Ovaries: Superior. Pollen color: Yellow.

Disease resistance: No disease problems noted to date.

General observations: Don Juan is principally characterized by its large, semi-double to double lavender colors borne on erect peduncles well above the contrasting dark green foliage.

I claim:

1. A new and distinct cultivar of African violet known by the cultivar name Don Juan, as described and illustrated, and particularly characterized by its semi-double to double lavender flowers carried on strong and erect peduncles so as to position the flower bouquet well above the dark foliage.

* * * * *

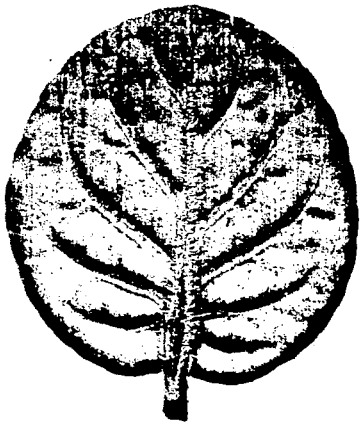
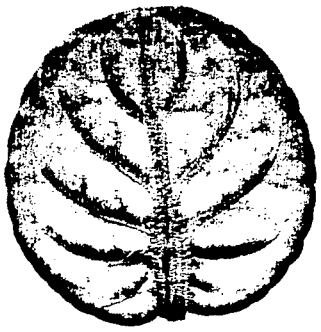
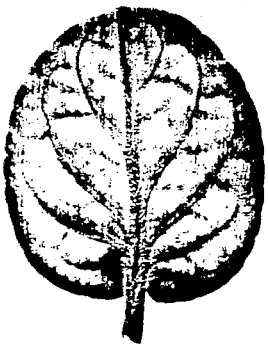
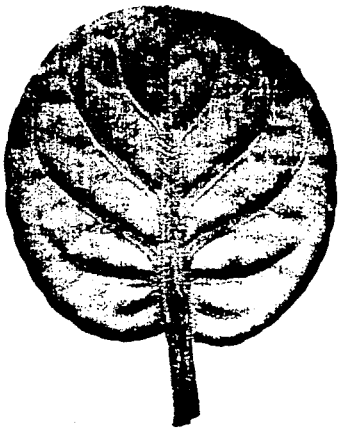

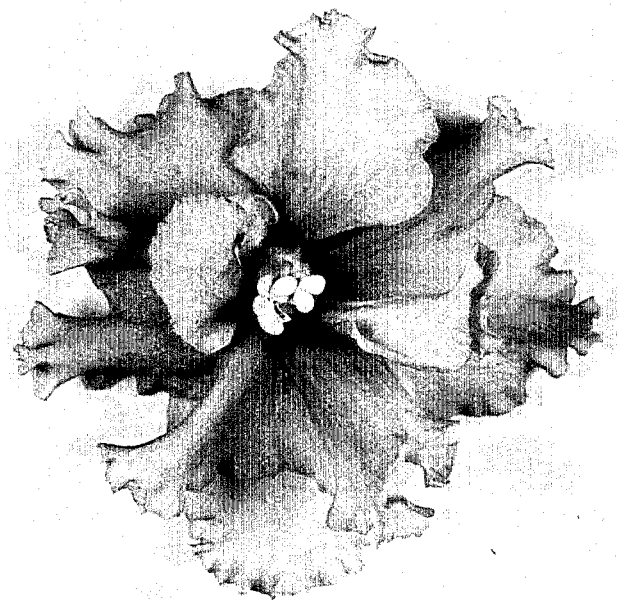

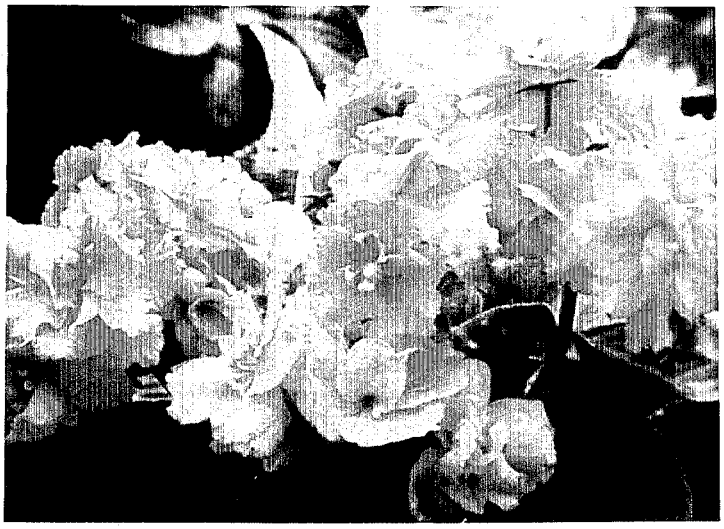
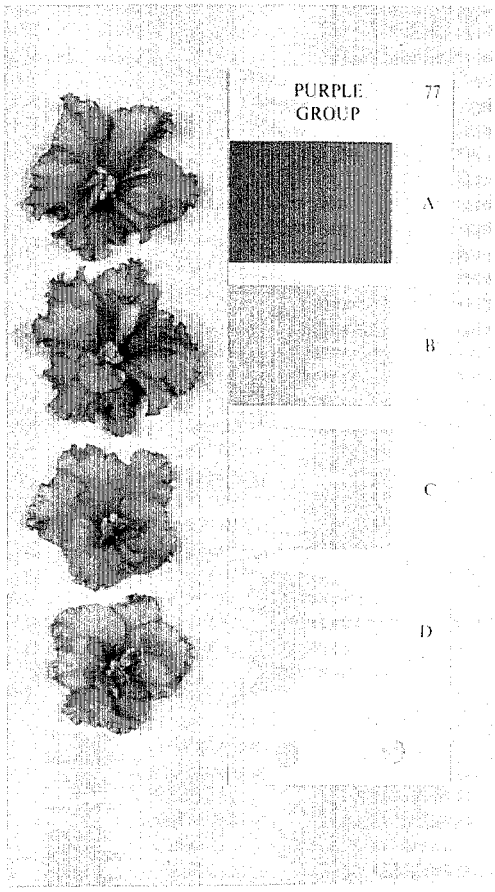
PURPLE
GROUP
77
A
B
C
D